US010940442B2

(12) United States Patent
    Mizobuchi et al.

(10) Patent No.: US 10,940,442 B2
(45) Date of Patent: Mar. 9, 2021

(54) COATINGS FOR BIOLOGICAL FLUID FILTERS

(71) Applicant: Fenwal, Inc., Lake Zurich, IL (US)

(72) Inventors: Yoshikazu Mizobuchi, Mundelein, IL (US); Jo Anne Alfaro, Arlington Heights, IL (US)

(73) Assignee: FENWAL, INC., Lake Zurich, IL (US)

(*) Notice: Subject to any disclaimer, the term of this patent is extended or adjusted under 35 U.S.C. 154(b) by 698 days.

(21) Appl. No.: 15/137,894

(22) Filed: Apr. 25, 2016

(65) Prior Publication Data

US 2016/0236152 A1    Aug. 18, 2016

Related U.S. Application Data

(62) Division of application No. 13/918,926, filed on Jun. 15, 2013.

(51) Int. Cl.
    *A61M 1/34*      (2006.01)
    *A61M 1/36*      (2006.01)
    (Continued)

(52) U.S. Cl.
    CPC ....... *B01D 67/0088* (2013.01); *A61M 1/0218* (2014.02); *A61M 1/3496* (2013.01); *A61M 1/3633* (2013.01); *B01D 29/0018* (2013.01); *B01D 69/02* (2013.01); *B01D 71/26* (2013.01); *B01D 71/38* (2013.01); *B01D 71/76* (2013.01); *A61M 2202/0439* (2013.01); *A61M 2207/00* (2013.01); *B01D 2239/0471* (2013.01); *B01D 2239/0478* (2013.01);
    (Continued)

(58) Field of Classification Search
    CPC .............. A61M 1/0218; A61M 1/0281; A61M 1/3633; A61M 1/3635; A61M 1/16; A61M 2202/0439; A61M 1/3496; A61M 2207/00; B01D 71/26; B01D 71/80; B01D 67/0088; B01D 71/38; B01D 29/0018; B01D 2323/22; B01D 2323/08; B01D 2323/12; B01D 2239/0478; B01D 2239/0622; B01D 2239/0471
    See application file for complete search history.

(56) References Cited

U.S. PATENT DOCUMENTS 5,351,698 A * 10/1994 Wheeler ............... A61F 6/04
                                                    128/844
5,726,212 A    3/1998 Yuk et al.
(Continued)

FOREIGN PATENT DOCUMENTS

EP    0498414 A2    8/1992
EP    1262204 A1    12/2002
(Continued)

OTHER PUBLICATIONS

Extended European Search Report dated Dec. 3. 2014 for European Patent Application No. 13194898.6-1356 (EP Patent No. 2818189).

*Primary Examiner* — Angel Olivera
(74) *Attorney, Agent, or Firm* — Cook Alex Ltd.

(57) ABSTRACT

Filter media, filter devices and methods of making filter media are disclosed. The filter media includes a coating on at least a portion of said outer surface. The coating may be polymeric composition having a molecular chain that includes segments of non-polar groups and segments of at least one of polar groups or segments of ionic groups.

17 Claims, 2 Drawing Sheets

(51) Int. Cl.

| | | |
|---|---|---|
| *B01D 29/00* | (2006.01) | |
| *B01D 67/00* | (2006.01) | |
| *B01D 69/02* | (2006.01) | |
| *B01D 71/26* | (2006.01) | |
| *B01D 71/38* | (2006.01) | |
| *B01D 71/76* | (2006.01) | |
| *A61M 1/02* | (2006.01) | |

(52) U.S. Cl.
CPC .. *B01D 2239/0622* (2013.01); *B01D 2323/08* (2013.01); *B01D 2323/12* (2013.01); *B01D 2323/22* (2013.01); *B01D 2325/02* (2013.01)

(56) References Cited

U.S. PATENT DOCUMENTS

| | | | |
|---|---|---|---|
| 2002/0113003 A1 | 8/2002 | Lynn et al. | |
| 2006/0207937 A1* | 9/2006 | Bonaguidi | A61M 1/3633 210/645 |
| 2007/0128512 A1* | 6/2007 | Kaimai | B01D 69/12 429/144 |
| 2007/0274887 A1* | 11/2007 | Scialla | A61L 9/015 423/210 |
| 2009/0098359 A1* | 4/2009 | Waller, Jr. | C08J 7/18 428/308.4 |
| 2012/0073791 A1 | 3/2012 | Dubois | |

FOREIGN PATENT DOCUMENTS

| | | |
|---|---|---|
| JP | 2006-133483 | 5/2006 |
| JP | 2013-57427 | 3/2013 |
| WO | WO 2004/064980 A1 | 8/2004 |
| WO | WO 2012/115021 A1 | 8/2012 |

\* cited by examiner

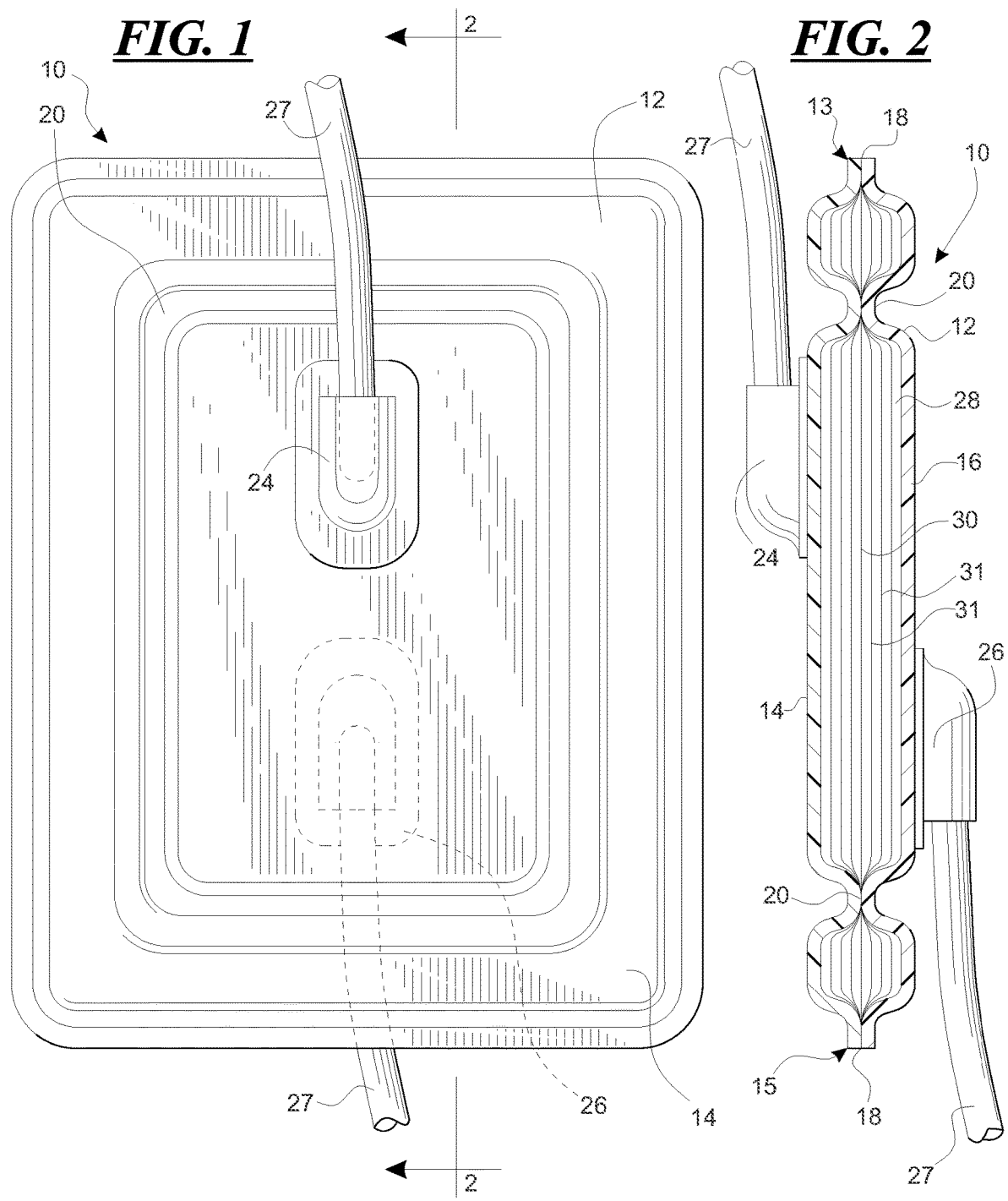

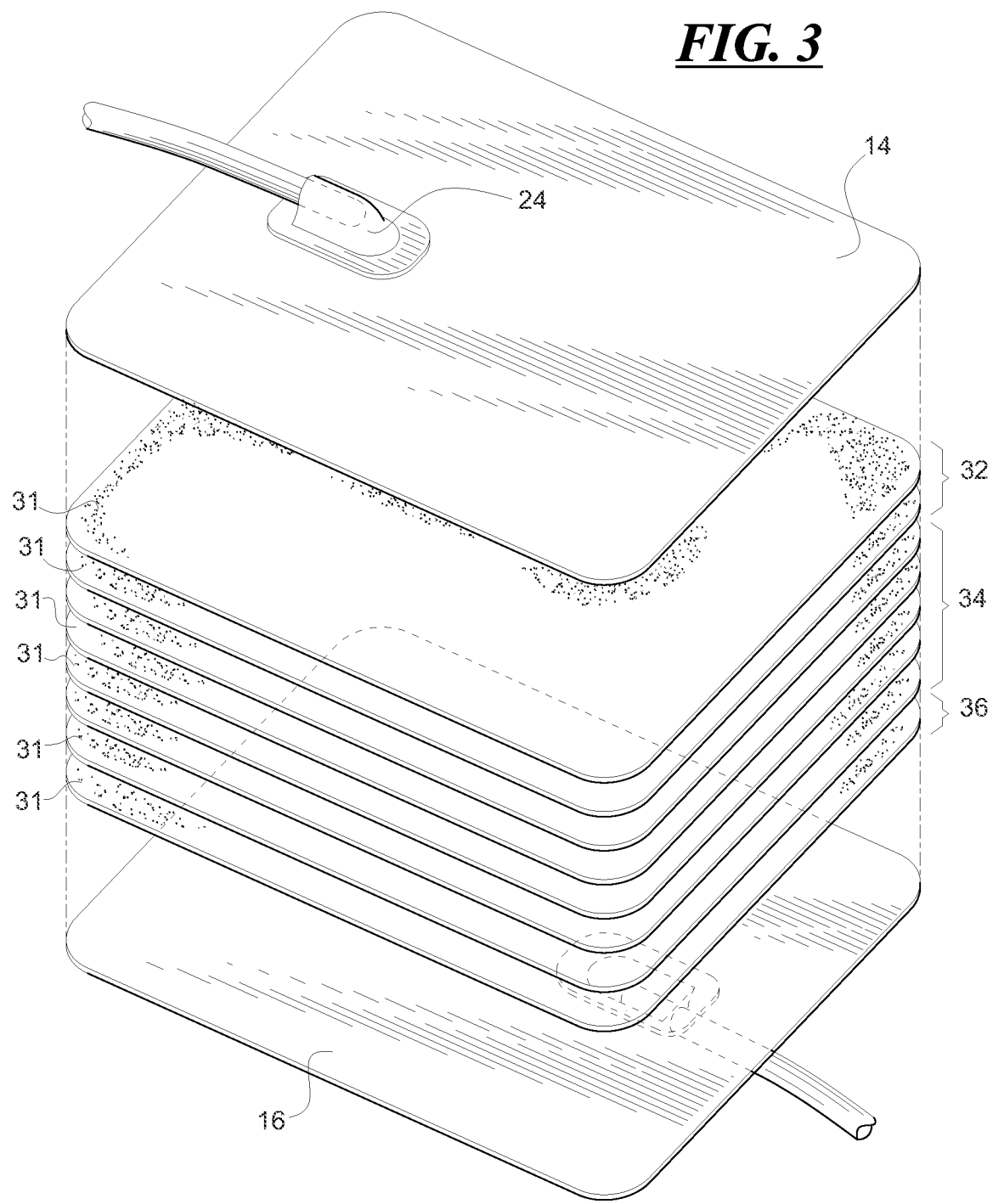

US 10,940,442 B2

COATINGS FOR BIOLOGICAL FLUID FILTERS

CROSS REFERENCE TO RELATED APPLICATION

This application is a divisional of U.S. application Ser. No. 13/918,926, filed Jun. 15, 2013, now abandoned, the entire contents of which is herein incorporated by reference.

FIELD OF THE DISCLOSURE

The present disclosure is directed to filters for use in the processing of biological fluids. More particularly, the present disclosure is directed to filters for removing white blood cells (leukocytes) from a biological fluid such as blood. Even more particularly, the present disclosure is directed to leukoreduction filters including a coating of a polymeric composition that enhances the wetting capability of the filter and the interaction of the filter with leukocytes.

BACKGROUND

Filters are commonly used in the medical field for removing unwanted components, agents or particulates from a biological fluid. In the field of blood processing and collection, it is common to remove leukocytes from the biological fluid or blood prior to transfusion of the collected blood to a patient. Leukocytes present in transfused blood can often cause adverse reactions in the patients receiving the transfusion.

Filtration requires passage of the biological fluid through a filter medium that retains the undesired leukocytes and other components or aggregates while allowing the remaining desirable components to pass through the medium and be collected for subsequent transfusion. The filter medium must be sufficiently wettable such that fluid can flow through the medium. Also, the filter medium must be sufficiently attracting of leukocytes or other target cells.

Leukoreduction and leukofiltration remain a keen area of interest in the field of blood processing. Accordingly, efforts to provide filters that are effective in removing as many leukocytes as possible from a biological fluid in a reduced time and in an efficient manner are ongoing.

SUMMARY

In one aspect, the present disclosure is directed to a filter medium. The filter medium includes a filter sheet having an outer surface and a coating on at least a portion of said outer surface. The coating may be polymeric composition having a molecular chain that includes segments of non-polar groups and segments of at least one of polar groups or segments of ionic groups.

In another aspect, the present disclosure is directed to a filtration device for processing biological fluid. The device includes a housing defining an interior chamber and an inlet port and an outlet port communicating with said chamber. The device also includes a filter medium within the chamber. The filter medium includes a filter sheet having an outer surface and a coating on at least a portion of said outer surface. The coating may be a polymeric composition having a molecular chain that includes segments of non-polar groups and segments of at least one of polar groups or segments of ionic groups.

In a further aspect, the present disclosure is directed to a method of making a leukoreduction filter. The method includes forming a coating material by dissolving a selected amount of a polymeric composition including segments of a non-polar groups and at least one of segments of polar groups or segments of ionic groups in a solvent. The method also includes contacting at least a portion of a porous material with the coating.

BRIEF DESCRIPTION OF THE DRAWINGS

FIG. 1 is a plan view of a representative leukoreduction filter;

FIG. 2 is a cross-sectional side view of a representative leukoreduction filter; and FIG. 3 is an exploded view of a representative leukoreduction filter including a plurality of filter sheets.

DETAILED DESCRIPTION OF THE EMBODIMENTS

FIG. 1 shows a representative leukoreduction filter that may be used in accordance with the present disclosure. Filter 10 is suited for removal of selected components from a biological fluid such as blood. Filter 10 includes housing 12, which includes outer walls 14 and 16. Housing 12 and, indeed, filter 10 are preferably made of a biocompatible material that is also sterilizable using conventional sterilization techniques commonly used in the assembly of disposable blood processing sets such as autoclaving, gamma-ray and/or electron-beam. In one embodiment, housing walls 14, 16 may be made of a rigid, polymeric material sealed at or near the periphery thereof. The sealing of walls 14, 16 may be achieved by adhesive, welding or other forms of sealing attachment.

In a preferred embodiment, as shown in FIG. 1, housing walls 14 and 16 may be made of a soft, flexible polymeric material. Examples of suitable polymeric materials for housing walls 14 and 16 include polyvinyl chloride and/or polyolefin. As shown in FIGS. 1 and 2, housing walls 14 and 16 may be joined along their peripheral edges to form a seal 18. In the embodiment of FIGS. 1 and 2, an additional inner peripheral seal 20 may also be provided, as described in U.S. Patent Application Publication US 2002/0113003, the contents of which are incorporated herein by reference. Seals 18 and 20 define a cushioned peripheral portion.

Typically, filters of the type described herein may be included as part of a disposable fluid processing set or kit where, in its most basic form, the biological fluid is introduced from a connected or pre-connected source, passed through the filter 10 and collected in a pre-attached container after it has passed through the membrane and the undesirable components captured by the filter medium. Thus, walls 14 and 16 may include inlet and outlet ports 24 and 26, respectively, to allow for introduction and exit of the fluid. Ports 24 and 26 communicate with an internal chamber 28, defined by walls 14 and 16. Ports 24 and 26 may be carried by walls 14 and 16, as shown in FIGS. 1 and 2. Ports 24 and 26 may be separately attached to housing walls 14, 16 or integrally molded with housing walls 14 and 16. As shown in FIGS. 1 and 2, the inlet and outlet ports 24 and 26 may be located in a diametrically opposed relationship on walls 14 and 16. Thus, for example, inlet port 24 may be positioned closer to the "top" peripheral edge 13 of filter 10 on wall 14, whereas outlet port 26 may be positioned closer to the "bottom" peripheral edge 15 of filter 10 and wall 16. Of course, it will be appreciated that the relative locations of ports 14 and 16 may be otherwise modified or provided. Ports 24 and 26 define internal flow paths which establish fluid communication between interior chamber 28 and tubing 27 leading to other containers or parts of a disposable processing set in which filter 10 is included.

As shown in FIG. 2, chamber 28 accommodates a filter medium 30. In one embodiment, filter 30 may be provided as a pad that includes a plurality of pores sized to prevent passage of leukocytes while allowing other desirable blood components to pass. In one embodiment, as shown in FIGS. 2 and 3, filter medium 30 may include a plurality of sheets 31 wherein each sheet 31 includes pores of a desired diameter and/or size and distribution. In one embodiment, sheets 31 may be made of melt blown, non-woven fibers. In accordance with the present disclosure, the fibers may be made of a suitable polymeric material, such as polyethylene or polypropylene or other polyolefin. In one embodiment, the polyolefin may be hydrophobic.

As shown in FIGS. 2 and 3, filter medium 30 may be made of a plurality of melt blown, non-woven fiber sheets. In addition, groups of sheets may provide a filter medium with filter portions selected to perform particular functions. For example, filter medium 30 may include a filter portion made up of a plurality of sheets wherein the filter portion 32 and/or the sheets that make up portion 32 adjacent or closest to housing wall 14 and inlet port 24 has/have a selected porosity that provides for the removal of microaggregates and smaller sized particulates. Although FIG. 3 shows only two sheets (for representative purposes only), portion 32 may include more than two sheets and may typically include, but is not limited to, 1 to 5 sheets to provide a "pre-filter."

Filter portion 34 may provide the primary or main filter and may likewise include a plurality of sheets of selected porosity. Although only 5 sheets are shown (for representative purposes only), the number of sheets that make up the primary or main filter may be anywhere from 10 to 30, wherein each sheet has a thickness of approximately 10 µm to 500 µm.

Filter portion 36 may provide for the filtration of additional components and/or serve as a spacer element between filter portion 34 and housing wall 16. Filter portion 36 which may also include a plurality of sheets (although only 1 sheet is shown for representative purposes only) is positioned downstream of filter portion 34 closer to housing wall 16 and outlet port 26. Portions 32, 34 and 36 may be brought together and sealed together to provide a unitary filter pad, i.e., filter medium 30. Alternatively, some or all of the individual sheets of each of the filter portions 32, 34 and 36 may be brought together and sealed at inner seal 20 with housing walls 14 and 16, as shown in FIG. 2.

The above-described embodiments are representative of an embodiment of a leukoreduction filter. Other filter structures may be possible which include more or fewer filter layers or filter portions.

In an embodiment, filter medium 30 includes a coating for enhancing the leukoreduction capability of filter 10 and interaction of the filter medium 30 with leukocytes. The coating is preferably a biocompatible polymeric composition that is capable of withstanding sterilization by autoclaving without degradation. In one embodiment, the coating includes a polymeric composition wherein the molecular chain of the composition includes non-polar groups and one of either polar groups or ionic groups. Preferably, the polymeric composition is a block co-polymer wherein the molecular chain includes repeating units of the non-polar group and one of either polar groups or ionic groups. Preferably, the block co-polymer is non-randomized.

In one embodiment, the non-polar groups of the molecular chain that make up the polymeric composition are olefins. Olefins that are useful in the coating composition of the present disclosure are typically polyethylene, polypropylene or polybutylene. The polar groups in the molecular chain of the polymeric composition are preferably vinyl groups, such as vinyl acetate. Thus, in one embodiment, the polymeric composition is a block co-polymer wherein the molecular chain includes ethylene or propylene or other polyolefin with groups of vinyl acetate. In one embodiment, the coating composition is poly (ethylene-co-vinyl acetate).

In another embodiment, where the polymer includes olefin (e.g., ethylene, propylene or butylene) and ionic groups, the ionic group may be selected from the group of organic acids including, preferably, acrylic acid. Accordingly, in one embodiment, the polymeric composition is a block co-polymer wherein the molecular chain includes groups of polyethylene or polypropylene or other polyolefin and groups of acrylic acid. In one embodiment, the coating composition is poly (ethylene-co-acrylic acid).

In the embodiment where the polymeric composition includes a block copolymer of olefin and vinyl acetate, vinyl acetate may be present in an amount of approximately 25%-75% by weight of the polymeric composition. In a more preferred embodiment, the vinyl acetate may be present in an amount between approximately 30% and 60% by weight of the polymeric composition, or more preferably, 30%-50% by weight of the polymeric composition. In a further preferred embodiment, the vinyl acetate may be present in the polymeric composition in an amount of approximately 40% by weight of the polymeric composition.

In an embodiment where the polymeric composition is a block co-polymer that includes olefin and acrylic acid, the amount of acrylic acid may be present in an amount of approximately 5%-50% by weight of the polymeric composition. More preferably, the acrylic acid may be included in an amount of between 10% and 40% by weight of the polymeric composition and, more preferably, 10% and 30% by weight of the polymeric composition. In a further preferred embodiment, acrylic acid may be present in an amount of approximately 20% by weight of the polymeric composition.

Coatings of the type described above may be applied to the filter pad (i.e., filter medium 30) or one or more, or all of the individual sheets that make up filter medium 30 by dip coating, spray coating or other forms of coating. Preferably, the thickness of the coating applied to the filter pad or filter sheets of filter medium 30 is such that it does not destruct the porous characteristics of the filter medium 30, and/or plug the pores in the filter medium 30.

Dip coating may be a preferred form of applying the coating to the filter medium 30 or the individual sheets of filter medium 30. Where the polymeric composition is a block co-polymer that includes olefin and vinyl acetate; the block co-polymer is preferably first dissolved in a suitable solvent. Suitable solvents in accordance with the present disclosure may include $C_6$ to $C_8$ aliphatic hydrocarbons, such as hexane, heptane and octane, and more particularly, hexane/2-butanone or hexane/ethanol. For example, where the polymeric composition is a block co-polymer of ethylene and vinyl acetate segments, the solvent may be hexane/2-butanone. In one non-limiting example, the ratio of hexane to 2-butanone may be 1:4. The concentration of the block co-polymer may be between 0.1 and 2.0 (w/v) and, more preferably, 0.14% 1.6% (w/v), including, but not limited to, 0.14%, 0.3%, 0.5%, 0.8% and 1.0% (w/v).

In an embodiment where the block co-polymer includes ethylene and acrylic acid, i.e., poly (ethylene-co-acrylic acid), the solvent may preferably be hexane/ethanol. In one specific, non-limiting example, the ratio of hexane to ethanol in the solvent may be 1:1. Furthermore, the concentration of the polymer in the solvent may be between 0.01%-2.0% (w/v) or more preferably between approximately 0.06%-1.0% (w/v), including, but not limited to, 0.06%, 0.14%, 0.3%, 0.5% and 1.0% (w/v).

Study

Seven layers of a polymer coated membrane were prepared. Some of the membranes were coated with a Type A co-polymer which was poly (ethylene-co-vinyl acetate), while others were coated with a Type B co-polymer which was poly (ethylene-co-acrylic acid). The underlying membranes were made of melt blown, non-woven polypropylene fibers. Different fiber diameters were tested, such as 0.9, 0.6 and 0.3 microns. Other details of the tested membrane are set forth in Table 1 below,

TABLE 1

| Type | Sample 1 | Sample 2 | Sample 3 |
|---|---|---|---|
| Materials | PP* | PP* | PP* |
| Fiber Diameter (mode) (μm) | 0.9 | 0.6 | 0.3 |
| Fiber Diameter (average) (μm) | 1.5 | 1.1 | 0.8 |
| Basis Weight (g/m2) | 15 | 15 | 15 |
| Thickness at 20 gf (mm) | 0.16 | 0.16 | 0.16 |
| Air Permeability (cc/cm$_2$/s) | 12 | 10 | 5.1 |
| Porosity (%) | 90 | 90 | 90 |
| Mean Pore Size (μm) | 7 | 5.6 | 3.3 |

*Polypropylene

The assembled 7-layer membranes were placed in a fixture and 3 ml of whole blood (fresh or held for 24 hours) were passed through the membrane at a rate of 10 ml per hour. Leukoreduction and platelet recovery were determined by calculating white blood cell counts at pre- and post-filtration using a Sysmex KX-21N Hematology Analyzer and (where the white cell count was at or near zero) a Becton Dickson FACScan Flow Cytometer. The results are reported below in Tables 2-5,

TABLE 2

Leukoreduction (%) of Membranes Coated
With Poly (ethylene-co-vinyl acetate)
Poly (ethylene-co-vinyl acetate) in Mixed
Solution of Hexane/2-Butanone (1/4 by Vol.)

| Polymer Concentration % | Sample 1 | Sample 2 | Sample 3 |
|---|---|---|---|
| Fresh Whole Blood | | | |
| 0.14 | | | |
| 0.3 | 92.64 | 99.86 | |
| 0.5 | | 99.94 | |
| 0.8 | 93.89 | 99.94 | |
| 1 | | 99.93 | |
| 24 Hr. RT Held Whole Blood | | | |
| 0.14 | | | 99.994 |
| 0.3 | | | |
| 0.5 | | 99.28 | |
| 0.8 | | 99.3 | |
| 1 | | 99.36 | |

TABLE 3

Platelet Reduction (%) of Membranes Coated
With Poly (ethylene-co-vinyl acetate)
Poly (ethylene-co-vinyl acetate) in Mixed
Solution of Hexane/2-Butanone (1/4 by Vol.)

| Polymer Concentration % | Sample 1 | Sample 2 | Sample 3 |
|---|---|---|---|
| Fresh Whole Blood | | | |
| 0.14 | | | |
| 0.3 | 100 | 99.3 | |
| 0.5 | | 100 | |
| 0.8 | 100 | 100 | |
| 1 | | 99.1 | |
| 24 Hr. RT Held Whole Blood | | | |
| 0.14 | | | |
| 0.3 | | | |
| 0.5 | | 100 | |
| 0.8 | | 100 | |
| 1 | | 99.9 | |

TABLE 4

Leukoreduction (%) of Membranes Coated
With Poly (ethylene-co-acrylic acid)
Poly (ethylene-co-acrylic acid) in Mixed
Solution of Hexane/Ethanol (1/1 by Vol.)

| Polymer Concentration % | Sample 1 | Sample 2 | Sample 3 |
|---|---|---|---|
| Fresh Whole Blood | | | |
| 0.06 | | | |
| 0.14 | 49.23 | 99.88 | 99.997 |
| 0.3 | 78.57 | 99.92 | 99.9999 |
| 0.5 | | 99.76 | |
| 1 | | 99.39 | |
| 24 Hr. RT Held Whole Blood | | | |
| 0.06 | | | 99.995 |
| 0.14 | | 98.7 | 99.98 |
| 0.3 | | 98.4 | |
| 0.5 | | 99.83 | |
| 1 | 89.89 | 98.56 | |

TABLE 5

Platelet Reduction (%) of Membranes Coated
With Poly (ethylene-co-acrylic acid)
Poly (ethylene-co-acrylic acid) in Mixed
Solution of Hexane/Ethanol (1/1 by Vol.)

| Polymer Concentration % | Sample 1 | Sample 2 | Sample 3 |
|---|---|---|---|
| Fresh Whole Blood | | | |
| 0.06 | | | |
| 0.14 | 89.4 | 99.3 | 34.1 |
| 0.3 | 93.2 | 99.5 | 17.7 |
| 0.5 | | 98.7 | |
| 1 | | 100 | |
| 24 Hr. RT Held Whole Blood | | | |
| 0.06 | | | |
| 0.14 | | 100 | 47.4 |
| 0.3 | | 99.7 | |
| 0.5 | | 100 | |
| 1 | 95.6 | 86.1 | |

Examples

Without limiting any of the foregoing, the subject matter described herein may be found in one or more apparatus or devices. For example in a first aspect of the present subject matter a filter medium is provided. The filter medium includes a filter sheet having an outer surface and a coating of a polymeric composition. The composition has a molecular chain with segments of non-polar groups and segments of at least one of polar groups or segments of ionic groups.

A second aspect of the present subject matter includes the device in accordance with the above-described first aspect wherein the segments of the nonpolar groups are olefins.

A third aspect of the present subject matter includes the device in accordance with the first or second aspect in which the segments of the polar groups are vinyl acetate.

A fourth aspect of the present subject matter includes the device in accordance with any one of the first or second aspects described above wherein the ionic group is acrylic acid.

A fifth aspect of the present subject matter includes the device in accordance with any one of the first through fourth aspects described above wherein the olefin is ethylene.

A sixth aspect of the present subject matter includes the device in accordance with any one of the first through fifth aspects described above wherein the olefin is hydrophobic.

A seventh aspect of the present subject matter includes the device in accordance with any one of the first through sixth aspect described above wherein the filter sheet is a melt blown, non-woven porous membrane.

An eighth aspect of the present subject matter includes the device in accordance with any one of the first through third or fifth through seventh aspects described above wherein the composition is a polymer of ethylene and vinyl acetate.

A ninth aspect of the present subject matter includes the device in accordance with the eighth aspect described above wherein the vinyl acetate makes up between about 5%-75%, by weight, of the polymeric composition A tenth aspect of the present subject matter includes the device in accordance with any one of the eighth or ninth aspects described above wherein the vinyl acetate makes up about 40%, by weight, of the polymeric composition.

An eleventh aspect of the present subject matter includes the device in accordance with any one of the first through tenth aspects described above including a pad that includes a plurality of the filter sheets.

A twelfth aspect of the present subject matter includes the device in accordance with any one of the first and second, fourth through seventh or eleventh aspects wherein the composition includes olefin and acrylic acid.

A thirteenth aspect of the present subject matter includes device in accordance with the twelfth aspect described above wherein the acrylic acid makes up between about 5%-50%, by weight, of the composition.

A fourteenth aspect of the present subject matter includes the device in accordance with any one of the twelfth or thirteenth aspects wherein the acrylic acid is present in an amount of about 20% of the polymeric composition.

A fifteenth aspect of the present subject matter includes the device in accordance with any one of the first through fourteenth aspects described above wherein the composition is a random polymer with a molecular chain that includes repeatable segments of the nonpolar and the at least one of the polar groups or ionic groups.

A sixteenth aspect of the present subject matter is a filtration device for processing biological fluid. The filtration device includes a housing defining an interior chamber and an inlet port and an outlet port communicating with the chamber. A filter media is within the chamber and the medium includes a coating of a polymeric composition. The polymeric composition has a molecular chain including segments of nonpolar groups and segments of at least one of a polar group or a segment of the ionic.

A seventeenth aspect of the present subject matter includes the device in accordance with the sixteenth aspect described above wherein the filter medium includes a plurality of sheets wherein at least one of the sheets includes the coding.

An eighteenth aspect of the present subject matter includes the device in accordance with any one of the sixteenth or seventeenth aspects described above wherein the segments of the nonpolar groups are olefins.

A nineteenth aspect of the present subject matter includes the device in accordance with any one of the sixteenth through eighteenth aspects wherein the segments of the polar groups are vinyl acetate.

A twentieth aspect of the present subject matter includes the device in accordance with any one of the sixteenth through eighteenth aspects wherein the segments of the ionic groups are acrylic acid.

A twenty-first aspect of the present subject matter includes the device in accordance with any one of the sixteenth through twentieth aspects described above wherein the filter medium is a melt blown, nonwoven porous membrane.

A twenty-second aspect of the present subject matter is a method of making a leukoreduction filter. The method includes forming a coating material by dissolving a selected amount of a polymeric composition that includes segments of nonpolar groups and at least one segment of a polar group or segment of ionic groups in a solvent. The method further includes contacting at least a portion of a porous material coating.

A twenty-third aspect of the present subject matter includes the method in accordance with twenty-second aspect described above where in the segments of the polar groups are vinyl acetate.

A twenty-fourth aspect of the present subject matter includes the method in accordance with the twenty-second and twenty-third aspects wherein the solvent comprises a mixture of hexane and 2-butanone.

A twenty-fifth aspect of the present subject matter includes the method in accordance with the twenty-fourth aspect described above wherein the ratio of the volume of hexane to the volume of 2-butanone is about 1:4.

A twenty-sixth aspect of the present subject matter includes the method in accordance with any one of the twenty-second through twenty-fifth aspects wherein the concentration of the polymeric composition in the solvent is between about 0.1%-2.0% (w/v).

A twenty-seventh aspect of the present subject matter includes the method in accordance with any one of the twenty-second through twenty sixth aspects wherein the concentration of the polymeric composition in the solvent is between about 0.14%-1.6% (w/v).

A twenty-eight aspect of the present subject matter includes the method in accordance with the twenty-second aspect described above wherein the segments of the ionic groups include acrylic acid.

A twenty-ninth aspect of the present subject matter includes the method in accordance with the twenty-eighth aspect described above wherein the solvent includes a mixture of hexane and ethanol.

A thirtieth aspect of the present subject matter includes the method in accordance with the twenty-ninth aspect described above wherein the ratio of the volume of hexane to the volume of ethanol is about 1:1.

A thirty-first aspect of the present subject matter includes the method in accordance with any one of the twenty-eight through thirtieth aspects described above wherein the concentration of the polymeric composition in the solvent is between about 0.1%-2.0% space (w/v).

A thirty second aspect of the present subject matter includes the method of any one of the twenty-eighth through thirty-first aspect described above wherein the concentration of the polymeric composition and the solvent is between about 0.06%-1.0% (w/v).

A thirty-third aspect of the present subject matter includes the method in accordance with any one of the twenty second through thirty-second aspects described above wherein the porous membrane is a melt blown, nonwoven porous membrane.

A thirty-fourth aspect of the present subject matter includes the method in accordance with the thirty-third aspect described above wherein the melt blown, non-woven porous membrane is substantially polyolefin.

A thirty-fifth aspect of the present subject matter includes the method in accordance with any one of the twenty-second through thirty-fourth aspects described above including drying the coded material under ambient conditions or elevated temperature.

A thirty-sixth aspect of the present subject matter includes the method in accordance with any one of the twenty-third through thirty-fifth aspects described above including drying the coded material in a convection type of an at 80° C. for about 30 minutes.

A thirty-seventh aspect of the present subject matter includes the method in accordance with any one of the twenty-second through thirty-sixth aspects including introducing the coded porous material between opposed walls of the housing.

It should be understood that various changes and modifications to the embodiments described herein will be apparent to those skilled in the art. Such changes and modifications can be made without departing from the spirit and scope of the inventions disclosed herein.

The invention claimed is:

1. A method of making a leukoreduction filter comprising:
   a) forming a coating by dissolving polymeric composition consisting essentially of segments of ethylene groups and segments of vinyl acetate groups in a solvent wherein said solvent comprises a mixture of hexane and 2-butanone in a ratio of 1:4 and
   b) contacting at least a portion of a porous material with said formed coating.

2. The method claim 1 wherein the concentration of said polymeric composition in said solvent of hexane and 2-butanone is between 0.1%-2.0% (w/v).

3. The method of claim 1 wherein the concentration of said polymeric composition in said solvent is between 0.14%-1.6% (w/v).

4. The method of claim 1 wherein said porous material comprises a melt blown, non-woven porous membrane.

5. The method of claim 4 wherein said melt blown, non-woven porous membrane substantially comprises polyolefin.

6. The method of claim 1 further comprising drying said coated material under one of ambient conditions or above ambient temperature.

7. The method of claim 1 further comprising drying said coated material in a convection type oven at 80° C. for up to 30 minutes.

8. The method of claim 1 further comprising introducing said coated porous material in between opposed walls of a housing.

9. The method of claim 1 further comprising drying said coated material in a convection type oven at 80° C. for more than 30 minutes.

10. The method of claim 1 comprising contacting at least a portion of a porous material with said coating by dip coating.

11. A method of making a leukoreduction filter comprising:
    a) forming a coating by dissolving a selected amount of a polymeric composition comprising consisting essentially of segments of ethylene groups and segments of acrylic groups in a solvent wherein said solvent comprises a mixture of hexane and ethanol in a ratio of 1:1 wherein the concentration of said polymeric composition in said solvent is between about 0.01%-0.5% (w/v); and
    b) contacting at least a portion of a porous material comprising a polyolefin selected from the group of polyethylene and polypropylene with said formed coating.

12. The method of claim 11 wherein said porous material comprises a melt blown, non-woven porous membrane substantially comprises polyolefin.

13. The method of claim 11 further comprising drying said coated material under one of ambient conditions or above ambient temperature.

14. The method of claim 11 further comprising drying said coated material in a convection type oven at 80° C. for up to 30 minutes.

15. The method of claim 11 further comprising introducing said coated porous material in between opposed walls of a housing.

16. The method of claim 11 further comprising drying said coated material in a convection type oven at 80° C. for more than 30 minutes.

17. The method of claim 11 comprising contacting at least a portion of a porous material with said coating by dip coating.

* * * * *